United States Patent
Shin et al.

(10) Patent No.: US 12,419,557 B2
(45) Date of Patent: Sep. 23, 2025

(54) PRESSURE SENSOR ARRAY FOR URODYNAMIC TESTING AND A TEST APPARATUS INCLUDING THE SAME

(71) Applicant: KOREA ELECTRONICS TECHNOLOGY INSTITUTE, Seongnam-si (KR)

(72) Inventors: Kyu Sik Shin, Seoul (KR); Yeon Hwa Kwak, Seoul (KR); Cheol Ung Cha, Seoul (KR)

(73) Assignee: KOREA ELECTRONICS TECHNOLOGY INSTITUTE, Seongnam-si (KR)

( * ) Notice: Subject to any disclaimer, the term of this patent is extended or adjusted under 35 U.S.C. 154(b) by 856 days.

(21) Appl. No.: 17/569,310

(22) Filed: Jan. 5, 2022

(65) Prior Publication Data

US 2023/0157603 A1 May 25, 2023

Related U.S. Application Data

(63) Continuation of application No. PCT/KR2021/020018, filed on Dec. 28, 2021.

(30) Foreign Application Priority Data

Nov. 24, 2021 (KR) ........................ 10-2021-0163525

(51) Int. Cl.
*A61B 5/20* (2006.01)
*A61B 5/00* (2006.01)
*A61M 25/00* (2006.01)

(52) U.S. Cl.
CPC ............ *A61B 5/205* (2013.01); *A61B 5/4381* (2013.01); *A61B 5/6852* (2013.01);
(Continued)

(58) Field of Classification Search
CPC ...... A61B 5/205; A61B 5/4381; A61B 5/6852; A61B 2562/0247; A61M 2025/0001
See application file for complete search history.

(56) References Cited

U.S. PATENT DOCUMENTS 4,873,990 A  10/1989  Holmes et al.

FOREIGN PATENT DOCUMENTS

| CN | 208784754 U | 4/2019 | |
| DE | 19522909 A1 * | 1/1997 | ......... A61B 1/00165 |

(Continued)

OTHER PUBLICATIONS

Office Action received in Korean Application No. 10-2021-0163525 dated Jul. 18, 2024.
(Continued)

*Primary Examiner* — Devin B Henson
*Assistant Examiner* — Erin Kathleen McCormack
(74) *Attorney, Agent, or Firm* — Knobbe, Martens, Olson & Bear, LLP

(57) ABSTRACT

This application relates to a pressure sensor array for urodynamic testing capable of simultaneously measuring bladder pressure, prostate pressure, and urethral pressure, and to a test apparatus including the pressure sensor array. In one aspect, the pressure sensor array for urodynamic testing is installed in a catheter and includes a base substrate having flexibility. The pressure sensor array may also include a bladder pressure sensor formed on a portion of the base substrate to be positioned in bladder and measuring bladder pressure. The pressure sensor array may further include a prostate pressure sensor formed on a portion of the base substrate to be positioned in prostate and measuring prostate pressure. The pressure sensor array may further include a
(Continued)

urethral pressure sensor formed on a portion of the base substrate to be positioned in urethra and measuring urethral pressure.

9 Claims, 6 Drawing Sheets

(52) U.S. Cl.
CPC . *A61B 2562/0247* (2013.01); *A61B 2562/043* (2013.01); *A61B 2562/164* (2013.01); *A61M 2025/0001* (2013.01); *A61M 25/0017* (2013.01)

(56) References Cited

FOREIGN PATENT DOCUMENTS

| | | | | |
|---|---|---|---|---|
| EP | 2637007 | * | 9/2013 | |
| KR | 10-2006-0127975 A | | 12/2006 | |
| KR | 10-2122891 B1 | | 6/2020 | |
| KR | 10-2020-0104827 A | | 9/2020 | |
| WO | WO-2009065940 A2 | * | 5/2009 | ............. A61B 5/205 |
| WO | WO-2020012857 A1 | * | 1/2020 | ........... A61B 5/0015 |
| WO | WO-2021205382 A1 | * | 10/2021 | ........... A61B 5/0031 |

OTHER PUBLICATIONS

Notice of Allowance received in Korean Application No. 10-2021-0163525 dated Feb. 20, 2025.

* cited by examiner

PRESSURE SENSOR ARRAY FOR URODYNAMIC TESTING AND A TEST APPARATUS INCLUDING THE SAME

CROSS REFERENCE TO RELATED APPLICATIONS

This is a continuation application of International Patent Application No. PCT/KR2021/020018, filed on Dec. 28, 2021, which claims priority to Korean patent application No. 10-2021-0163525 filed on Nov. 24, 2021, contents of both of which are incorporated herein by reference in their entireties.

BACKGROUND

Technical Field

The present disclosure relates to urodynamic testing. More particularly, the present disclosure relates to a pressure sensor array for urodynamic testing capable of simultaneously measuring bladder pressure, prostate pressure, and urethral pressure, and to a test apparatus including the pressure sensor array for urodynamic testing.

Description of Related Technology

Urinary dysfunction is a symptom observed in patients with various micturition disorders such as urinary incontinence, prostatic hyperplasia, prostate pressure, cystitis, and bladder pressure. In diagnosing urinary dysfunction, a questionnaire, physical examination, radiographic examination, endoscopy, and urodynamic testing (or referred to as urodynamic study) are selectively performed.

The urodynamic testing provides important information for diagnosing various urinary dysfunctions, such as dysuria, urinary incontinence, and neurogenic bladder, and determining the treatment policy. The urodynamic testing is an important test that helps a more accurate diagnosis of dysuria disease. The urodynamic testing has an advantage of objectively identifying the physiological functions and conditions of the lower urinary tract, which cannot be known through a questionnaire, physical examination, radiographic examination, and endoscopy, and is therefore a necessary test for patients with urinary incontinence or prostatic hyperplasia.

The urodynamic testing consists of three major tests: uroflowmetry, bladder pressure measurement, and sphincter function test.

The uroflowmetry is a test to determine whether there is a decrease in the detrusor contraction or obstruction of the bladder outlet in a patient who complains of difficulty urinating. The bladder pressure measurement examines the bladder function while recording pressure changes that occur during bladder filling and urination. The sphincter function test is performed through electromyography, urethral pressure measurement, or urine leakage pressure measurement to determine the function of the sphincter.

SUMMARY

An object of the present disclosure is to provide a pressure sensor array capable of performing urodynamic testing conveniently and quickly and a test apparatus including the pressure sensor array.

Another object of the present disclosure is to provide a pressure sensor array for urodynamic testing capable of simultaneously measuring bladder pressure, prostate pressure, and urethral pressure, and a test apparatus including the same.

In order to accomplish the above objects, the present disclosure provides a pressure sensor array for urodynamic testing installed in a catheter, the pressure sensor array including a base substrate having flexibility; a bladder pressure sensor formed on a portion of the base substrate to be positioned in bladder and measuring bladder pressure; a prostate pressure sensor formed on a portion of the base substrate to be positioned in prostate and measuring prostate pressure; and a urethral pressure sensor formed on a portion of the base substrate to be positioned in urethra and measuring urethral pressure.

The bladder pressure sensor, the prostate pressure sensor, and the urethral pressure-sensor are sequentially formed on the base substrate.

The bladder pressure sensor is an atmospheric pressure sensor for measuring absolute pressure in the bladder.

The prostate pressure sensor and the urethral pressure sensor are strain gauges for measuring pressure at which the prostate and urethra are tightened.

The bladder pressure sensor may be formed on an upper surface of the base substrate.

The prostate pressure sensor and the urethral pressure sensor may be formed on a lower surface of the base substrate.

The pressure sensor array for urodynamic testing according to the present disclosure may further include readout elements formed on an upper surface of the base substrate and respectively reading out pressures measured by the bladder pressure sensor, the prostate pressure sensor, and the urethral pressure sensor.

In addition, the present disclosure provides a urodynamic test apparatus that includes a catheter inserted into bladder through urethra and prostate; and a pressure sensor array installed in the catheter and measuring bladder pressure, prostate pressure, and urethral pressure.

The bladder pressure sensor protrudes out of a tip of the catheter.

The prostate pressure sensor and the urethral pressure sensor are located inside the catheter.

The pressure sensor array is installed in the catheter such that the lower surface of the base substrate is in close contact with an inner surface of the catheter.

According to the present embodiment, it is possible to simultaneously measure the bladder pressure, the prostate pressure, and the urethral pressure through the pressure sensor array provided in the catheter.

Because of having a structure that the pressure sensor array is inserted into the catheter, the urodynamic test apparatus according to the present embodiment is capable of simultaneously measuring the bladder pressure, the prostate pressure, and the urethral pressure while minimizing a structural change thereof.

DETAILED DESCRIPTION

Recently, a test method that simultaneously performs the uroflowmetry and the bladder pressure measurement has been implemented, and the electromyography and the imaging tests are sometimes performed selectively.

The urodynamic testing is very complex, and the process and technology are also complicated. So, a number of test modules are installed in and connected to the test equipment for the urodynamic testing, resulting in bulky and heavy.

Therefore, the urodynamic test equipment is almost impossible to move, so that the patient is to be tested next to it. In general, the hospital separately provides the urodynamic laboratory equipped with the urodynamic test equipment, and the patient is subjected to the urodynamic testing in the laboratory. That is, the patient mounts the test sensor module in a state where the test site is exposed next to the urodynamic test equipment in the laboratory, and receives the urodynamic testing.

In the following description, only parts necessary to understand embodiments of the present disclosure will be described, and other parts will not be described to avoid obscuring the subject matter of the present disclosure.

Terms used herein should not be construed as being limited to their usual or dictionary meanings. In view of the fact that the inventor can appropriately define the meanings of terms in order to describe his/her own disclosure in the best way, the terms should be interpreted as meanings consistent with the technical idea of the present disclosure. In addition, the following description and corresponding drawings merely relate to specific embodiments of the present disclosure and do not represent all the subject matter of the present disclosure. Therefore, it will be understood that there are various equivalents and modifications of the disclosed embodiments at the time of the present application.

Now, embodiments of the present disclosure will be described in detail with reference to the accompanying drawings.

Figure 1:
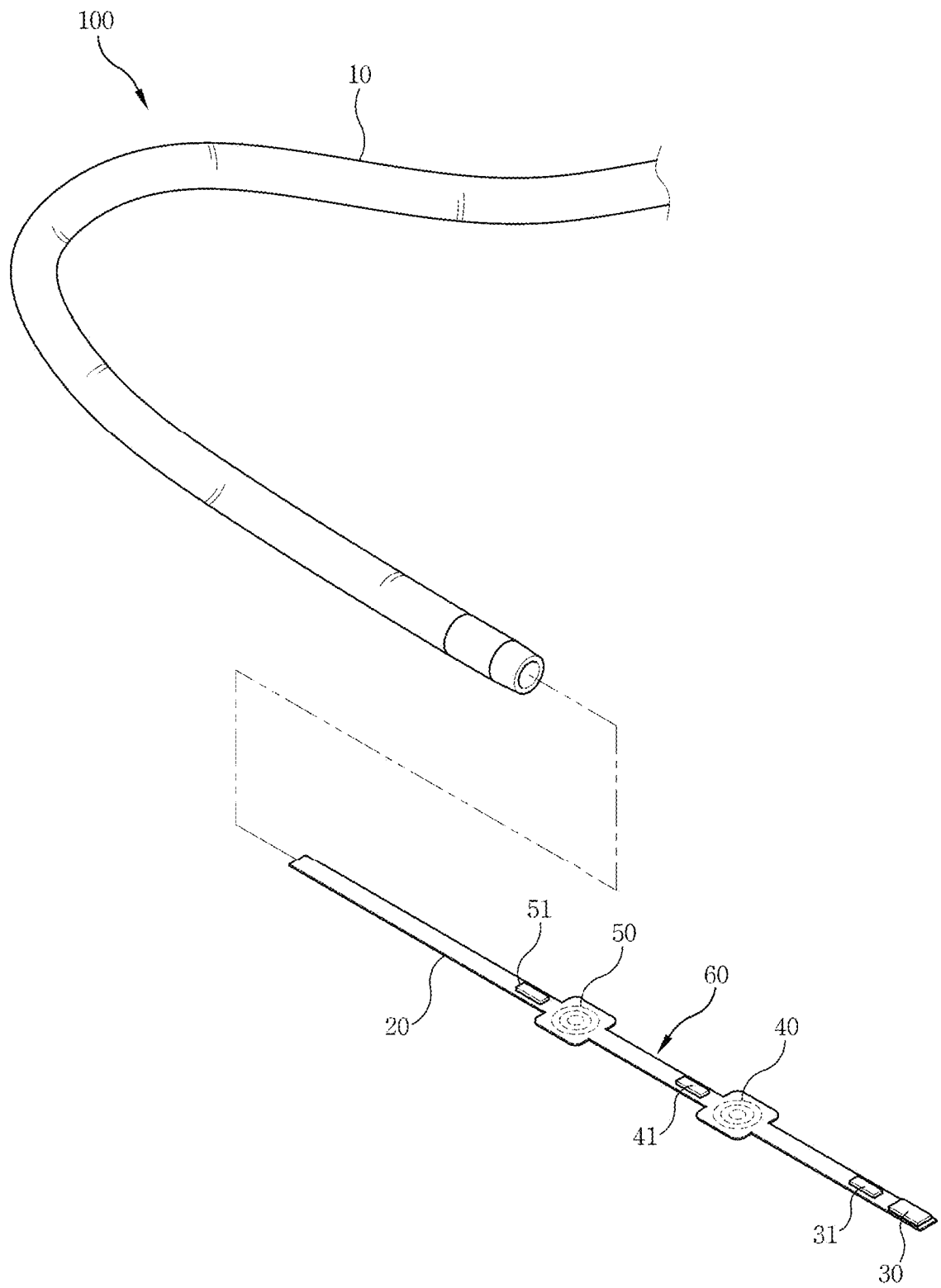
FIG. 1 is an exploded perspective view showing a test apparatus including a pressure sensor array for urodynamic testing according to an embodiment of the present disclosure.

FIG. 1 is an exploded perspective view showing a test apparatus including a pressure sensor array for urodynamic testing according to an embodiment of the present disclosure.

Figure 2:
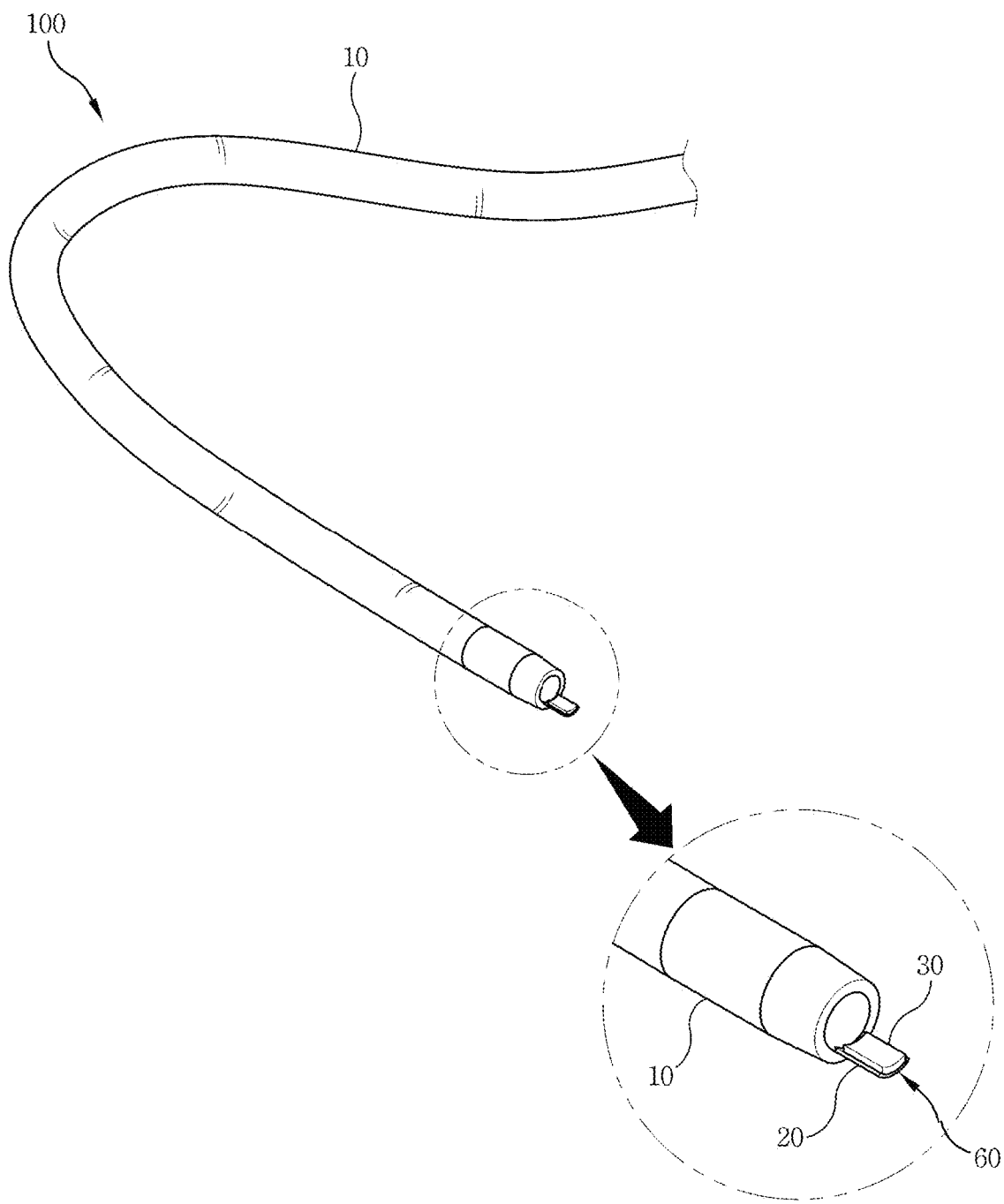
FIG. 2 is a combined perspective view showing the test apparatus of FIG. 1.

FIG. 2 is a combined perspective view showing the test apparatus of FIG. 1.

Referring to FIGS. 1 and 2, the urodynamic test apparatus 100 according to an embodiment is a test apparatus capable of measuring bladder pressure, prostate pressure, and urethral pressure which are required for urodynamic testing. The urodynamic test apparatus 100 according to this embodiment includes a catheter 10 and a pressure sensor array 60. The catheter 10 is inserted into the bladder through the urethra and the prostate. The pressure sensor array 60 is installed in the catheter 10 and measures bladder pressure, prostate pressure, and urethral pressure. The pressure sensor array 60 includes a base substrate 20 having flexibility and also includes a bladder pressure sensor 30, a prostate pressure sensor 40, and a urethral pressure sensor 50, which are formed on the base substrate 20. The bladder pressure sensor 30 is formed on a portion of the base substrate 20 to be positioned in the bladder, and measures the bladder pressure. The prostate pressure sensor 40 is formed on a portion of the base substrate 20 to be positioned in the prostate, and measures the prostate pressure. The urethral pressure sensor 50 is formed on a portion of the base substrate 20 to be positioned in the urethra, and measures the urethral pressure.

Because the pressure sensor array 60 is based on the base substrate 20 having flexibility, it can be installed by being inserted into the catheter 10 in a rolled form. The base substrate 20 has a shape of a narrow width and a long length.

The bladder pressure sensor 30 installed at a front portion of the pressure sensor array 60 protrudes out of the tip of the catheter 10 to measure the bladder pressure.

The prostate pressure sensor 40 and the urethral pressure sensor 50 are located inside the catheter 10. The prostate pressure sensor 40 and the urethral pressure sensor 50 measure, in the prostate and urethra, the pressure applied to the catheter 10 by urine discharged through the prostate and urethra from the bladder, thereby measuring the prostate pressure and the urethral pressure.

Figure 3:
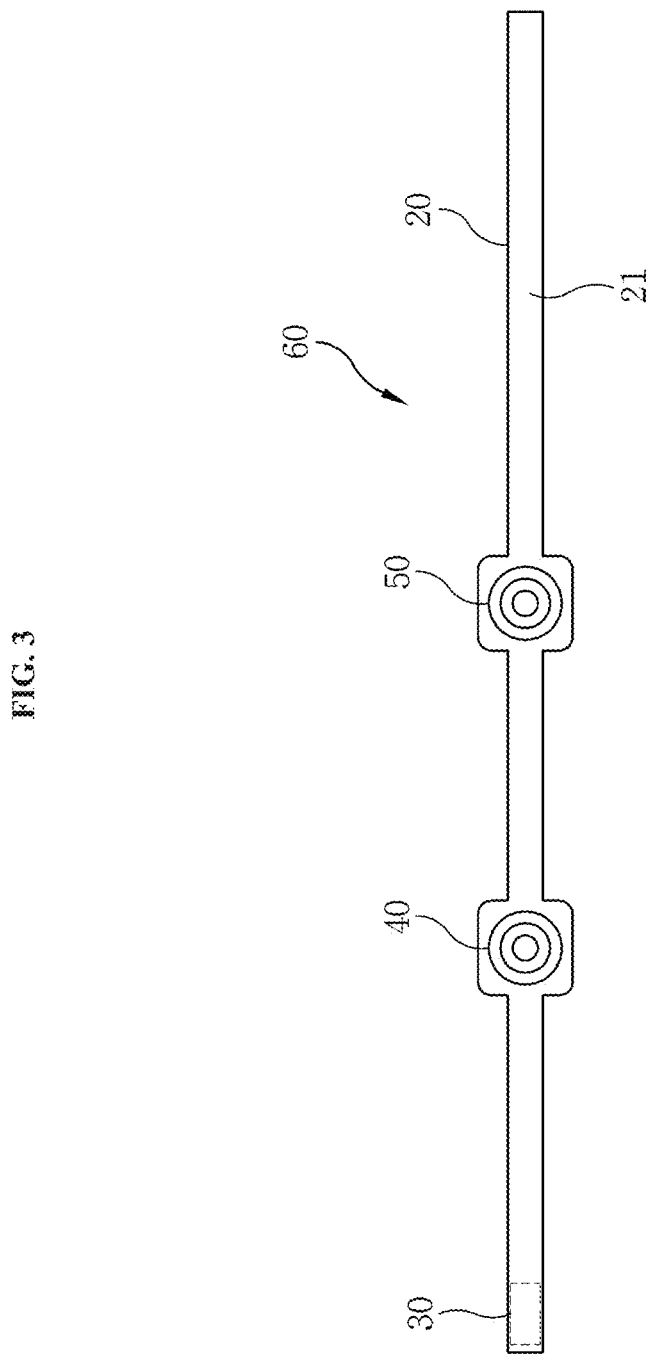
FIG. 3 is a plan view showing a lower surface of the pressure sensor array of FIG. 1.
Figure 4:
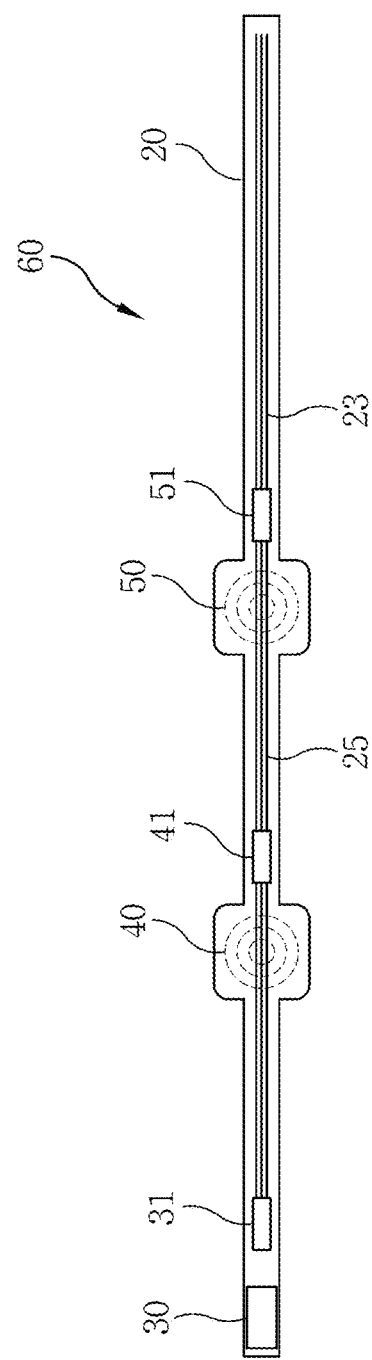
FIG. 4 is a plan view showing an upper surface of the pressure sensor array of FIG. 1.
Figure 5:
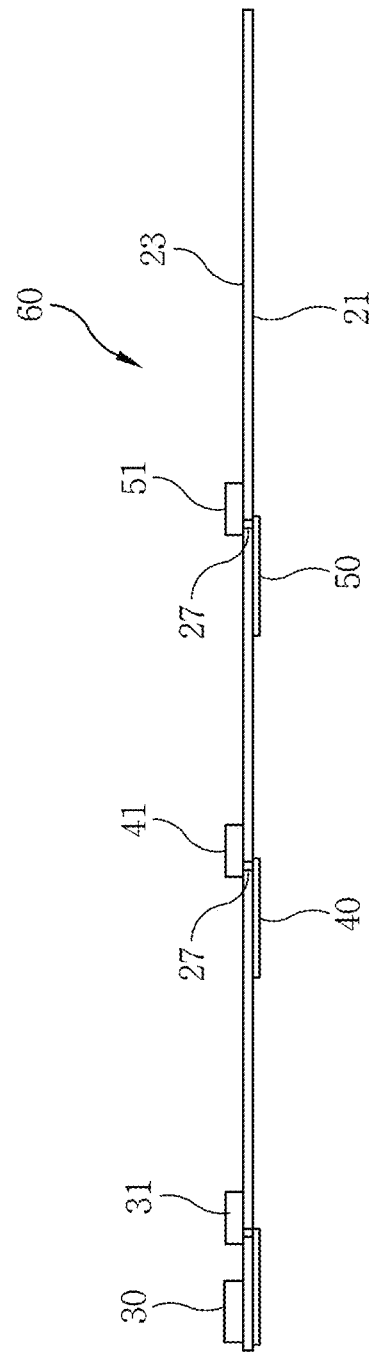
FIG. 5 is a cross-sectional view taken along line 5-5 of FIG. 3.
Figure 6:
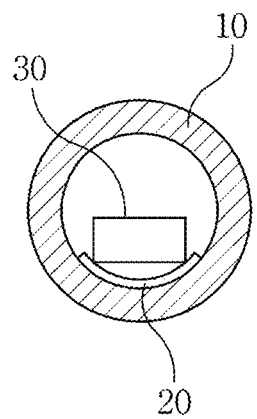
FIG. 6 is a cross-sectional view showing the bladder pressure sensor positioned outside a tip of the catheter.
Figure 7:
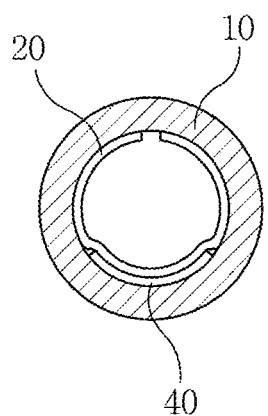
FIG. 7 is a cross-sectional view showing the prostate pressure sensor positioned inside the catheter.
Figure 8:
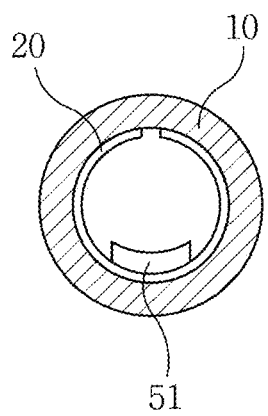
FIG. 8 is a cross-sectional view showing readout elements positioned inside the catheter.

Hereinafter, the pressure sensor array 60 according to this embodiment will be described in more detail with reference to FIGS. 3 to 8. FIG. 3 is a plan view showing a lower surface of the pressure sensor array 60 of FIG. 1. FIG. 4 is a plan view showing an upper surface of the pressure sensor array 60 of FIG. 1. FIG. 5 is a cross-sectional view taken along line 5-5 of FIG. 3. FIG. 6 is a cross-sectional view showing the bladder pressure sensor 30 positioned outside a tip of the catheter 10. FIG. 7 is a cross-sectional view showing the prostate pressure sensor 40 positioned inside the catheter 10. FIG. 8 is a cross-sectional view showing readout elements 31, 41, and 51 positioned inside the catheter.

The pressure sensor array 60 according to this embodiment includes the base substrate 20, the bladder pressure sensor 30, the prostate pressure sensor 40, and the urethral pressure sensor 50.

The base substrate 20 is a printed circuit board having flexibility and capable of transmitting pressure values measured by the bladder pressure sensor 30, the prostate pressure sensor 40, and the urethral pressure sensor 50 to an external controller through a circuit wiring 25.

The base substrate 20 may be formed of a plastic material having flexibility. The base substrate 20 has a lower surface 21 and an upper surface 23.

On the base substrate 20, the bladder pressure sensor 30, the prostate pressure sensor 40, and the urethral pressure sensor 50 are sequentially formed. In particular, the prostate pressure sensor 40 and the urethral pressure sensor 50 may be formed on the lower surface 21 of the base substrate 20, and the bladder pressure sensor 30 may be formed on the upper surface 23 of the base substrate 20.

The bladder pressure sensor 30 is an atmospheric pressure sensor that measures absolute pressure in the bladder. For example, the atmospheric pressure sensor may be a parylene-coated MEMS-based absolute pressure sensor.

The prostate pressure sensor 40 and the urethral pressure sensor 50 are strain gauges for measuring the pressure at which the prostate and urethra are tightened. The portions of the base substrate 20 on which the prostate pressure sensor 40 and the urethral pressure sensor 50 are formed may have a larger area than the other portions.

In addition, the pressure sensor array 60 according to this embodiment may further include readout elements 31, 41, and 51 (readout integrated circuits; ROICs). The readout elements 31, 41, and 51 are formed on the upper surface 23 of the base substrate 20 and respectively read out the pressures measured by the bladder pressure sensor 30, the prostate pressure sensor 40, and the urethral pressure sensor 50. In an example of this embodiment, the readout elements 31, 41, and 51 are connected to the bladder pressure sensor 30, the prostate pressure sensor 40, and the urethral pressure sensor 50, respectively.

The readout elements 31, 41, and 51 include a first readout element 31 connected to the bladder pressure sensor 30, a second readout element 41 connected to the prostate pressure sensor 40, and a third readout element 51 connected to the urethral pressure sensor 50.

When one of the bladder pressure sensor 30, the prostate pressure sensor 40, and the urethral pressure sensor 50 and a corresponding one of the first to third readout sensors are formed on different surfaces of the base substrate 20, they are electrically connected to each other through a via 27 passing through the base substrate 20. That is, because the prostate pressure sensor 40 and the urethral pressure sensor 50 are formed on the lower surface 21 of the base substrate 20, and the second and third readout elements 41 and 51 are formed on the upper surface 23 of the base substrate 20, the prostate pressure sensor 40 and the urethral pressure sensor 50 are electrically connected to the second and third readout elements 41 and 51 through the vias 27, respectively.

Because the bladder pressure sensor 30 and the first readout element 31 are formed on the same surface, the bladder pressure sensor 30 and the first readout element 31 may be electrically connected to each other through the circuit wiring 25.

The pressure sensor array 60 according to this embodiment may be installed in the catheter 10, as follows.

The pressure sensor array 60 is installed in the catheter 10 such that the lower surface 21 of the base substrate 20 is in close contact with the inner surface of the catheter 10. The bladder pressure sensor 30 is installed in the catheter 10 to protrude out of the tip of the catheter 10. An open portion of the tip of the catheter 10 from which the bladder pressure sensor 30 protrudes is sealed with a stopper or a sealing material.

In addition, the prostate pressure sensor 40 and the urethral pressure sensor 50 are positioned inside the catheter 10. At this time, the prostate pressure sensor 40 and the urethral pressure sensor 50 are installed in close contact with the inner surface of the catheter 10. The prostate pressure sensor 40 and the urethral pressure sensor 50 being in close contact with the inner surface of the catheter 10 measure, in the prostate and urethra, the pressure applied to the catheter 10 by urine discharged through the prostate and urethra from the bladder, thereby measuring the prostate pressure and the urethral pressure.

As described above, according to the present embodiment, it is possible to simultaneously measure the bladder pressure, the prostate pressure, and the urethral pressure through the pressure sensor array 60 provided in the catheter 10.

Because of having a structure that the pressure sensor array 60 is inserted into the catheter, the urodynamic test apparatus 100 according to the present embodiment is capable of simultaneously measuring the bladder pressure, the prostate pressure, and the urethral pressure while minimizing a structural change thereof.

While the present disclosure has been particularly shown and described with reference to an exemplary embodiment thereof, it will be understood by those skilled in the art that various changes in form and details may be made therein without departing from the scope of the present disclosure as defined by the appended claims.

What is claimed is:

1. A pressure sensor array for urodynamic testing installed in a catheter, the pressure sensor array comprising:
    a base substrate having flexibility, the base substrate comprising a lower surface and an upper surface opposing the lower surface, the base substrate comprises a first via hole and a second via hole spaced apart from each other and passing through the base substrate;
    a bladder pressure sensor formed on a portion of the base substrate to be positioned in bladder and configured to measure bladder pressure;
    a first readout element connected to the bladder pressure sensor and disposed adjacent to the bladder pressure sensor;
    a prostate pressure sensor formed on a portion of the base substrate to be positioned in prostate and configured to measure prostate pressure;
    a second readout element connected to the prostate pressure sensor and disposed closer to the prostate pressure sensor than the bladder pressure sensor;
    a urethral pressure sensor formed on a portion of the base substrate to be positioned in urethra and configured to measure urethral pressure; and
    a third readout element connected to the urethral pressure sensor and disposed closer to the urethral pressure sensor than the bladder pressure sensor and the prostate pressure sensor,
    wherein the third readout element, the urethral pressure sensor, the second readout element, the prostate pressure sensor, the first readout element, and the bladder pressure sensor are arranged in this order on the base substrate,
    wherein the prostate pressure sensor and the urethral pressure sensor are formed on the lower surface of the base substrate, and the bladder pressure sensor is formed on the upper surface of the base substrate,
    wherein the second readout element and the third readout element are formed on the upper surface of the base substrate and are respectively electrically connected to the prostate pressure sensor and the urethral pressure sensor, formed on the lower surface of the base substrate, via the first via hole and the second via hole,
    wherein the first readout element is formed on the upper surface of the base substrate,
    wherein the bladder pressure sensor and the first readout element are connected to each other via circuit wiring,
    wherein the prostate pressure sensor is formed in a first area of the base substrate,
    wherein the urethral pressure sensor is formed in a second area of the base substrate,
    wherein the bladder pressure sensor is formed in a third area of the base substrate, and
    wherein the third area is smaller than each of the first area and the second area.

2. The pressure sensor array for urodynamic testing of claim 1, wherein the bladder pressure sensor comprises an atmospheric pressure sensor configured to measure absolute pressure in the bladder.

3. The pressure sensor array for urodynamic testing of claim 2, wherein the prostate pressure sensor and the urethral pressure sensor comprise strain gauges configured to measure pressure at which the prostate and urethra are tightened.

4. A urodynamic test apparatus comprising:
   a catheter inserted into bladder through urethra and prostate; and
   the pressure sensor array of claim 1 installed in the catheter.

5. The urodynamic test apparatus of claim 4, wherein the bladder pressure sensor protrudes out of a tip of the catheter, and
   wherein the prostate pressure sensor and the urethral pressure sensor are located inside the catheter.

6. The urodynamic test apparatus of claim 4, wherein the bladder pressure sensor comprises an atmospheric pressure sensor configured to measure absolute pressure in the bladder, and
   wherein the prostate pressure sensor and the urethral pressure sensor comprise strain gauges configured to measure pressure at which the prostate and urethra are tightened.

7. The urodynamic test apparatus of claim 4, wherein the pressure sensor array is installed in the catheter such that the lower surface of the base substrate is in contact with an inner surface of the catheter.

8. The pressure sensor array for urodynamic testing of claim 1, wherein all of the first readout element, the second readout element, and the third readout element are located inside the catheter.

9. The pressure sensor array for urodynamic testing of claim 1, wherein all of the third readout element, the urethral pressure sensor, the second readout element, the prostate pressure sensor, the first readout element are located inside the catheter, and wherein the bladder pressure sensor is located outside the catheter.

* * * * *